(12) United States Patent
Gagnon

(10) Patent No.: US 9,193,760 B2
(45) Date of Patent: Nov. 24, 2015

(54) DISSOCIATION OF PRODUCT-COMPLEXED CONTAMINANTS IN CHROMATOGRAPHY

(75) Inventor: Peter S. Gagnon, Singapore (SG)

(73) Assignee: Bio-Rad Laboratories, Inc., Hercules, CA (US)

( * ) Notice: Subject to any disclaimer, the term of this patent is extended or adjusted under 35 U.S.C. 154(b) by 1100 days.

(21) Appl. No.: 13/237,294

(22) Filed: Sep. 20, 2011

(65) Prior Publication Data

US 2012/0252098 A1    Oct. 4, 2012

Related U.S. Application Data

(60) Provisional application No. 61/384,565, filed on Sep. 20, 2010.

(51) Int. Cl.
| | |
|---|---|
| C07K 1/00 | (2006.01) |
| C07K 1/18 | (2006.01) |
| B01D 15/38 | (2006.01) |
| C07K 1/22 | (2006.01) |
| B01D 15/36 | (2006.01) |

(52) U.S. Cl.
CPC .............. *C07K 1/18* (2013.01); *B01D 15/3828* (2013.01); *C07K 1/22* (2013.01); *B01D 15/362* (2013.01)

(58) Field of Classification Search
None
See application file for complete search history.

(56) References Cited

U.S. PATENT DOCUMENTS

| | | | | |
|---|---|---|---|---|
| 8,093,364 | B2 * | 1/2012 | Gagnon | ..................... 530/390.5 |
| 2009/0186396 | A1 | 7/2009 | Gagnon | |
| 2009/0187005 | A1 | 7/2009 | Gagnon | |
| 2009/0247735 | A1 * | 10/2009 | Gagnon | ........................ 530/413 |
| 2012/0027778 | A1 * | 2/2012 | Gurney | ..................... 424/172.1 |
| 2012/0077961 | A1 | 3/2012 | Gagnon | |
| 2012/0202975 | A1 * | 8/2012 | Cummings | ................ 530/388.1 |

FOREIGN PATENT DOCUMENTS

| | | |
|---|---|---|
| JP | 2003-528884 A | 9/2003 |
| WO | 01/72769 A2 | 10/2001 |
| WO | 2010/051360 A1 | 5/2010 |

OTHER PUBLICATIONS

Gagnon, P. et al., "IgM Purification," 4th International Monolith Summer School & Symposium, Portoroz, May 29-Jun. 2, 2010, 30 pages.
Gagnon, P. et al., "Reverse calcium affinity purification of Fab with calcium derivatized hydroxyapatite," Journal of Immunological Methods, Elsevier Science Publishers B.V., Amsterdam, NL, vol. 342, No. 1-2, Mar. 15, 2009, pp. 115-118.
Gagnon, P., "Phosphate-Free Buffer Systems A New Frontier for Apatite Chromatography," 4th International Conference on Hydroxyapatite, Sonoma, May 4-6, 2008, 36 pages.
Gagnon, P., "Production of Biobetter IgG with Enhanced Wash and Elution of Protein A," BIT 2nd International Congress of Antibodies, Beijing, Mar. 24-26, 2010, 37 pages.
Norstrom, T. et al., "Generation of a new protein purification matrix by loading ceramic hydroxyapatite with metal ions—demonstration with poly-histidine tagged green fluorescent protein," Journal of Biotechnology, Elsevier Science Publishers B.V., Amsterdam, NL, vol. 69, No. 2-3, Apr. 15, 1999, pp. 125-133.
Shukla, A. et al., "Host Cell Protein Clearance During Protein A Chromatography: Development of an Improved Column Wash Step," Biotechnol Progr, 2008, vol. 24, pp. 1115-1121.
International Search Report and Written Opinion issued in connection with corresponding International Application No. PCT/US2011/052377, mailed Jan. 12, 2012, 6 pages.
Extended European Search Report issued in connection with corresponding European Application No. EP 11827361, mailed Aug. 7, 2014, 7 pages.

* cited by examiner

*Primary Examiner* — Gary W Counts
(74) *Attorney, Agent, or Firm* — Kilpatrick Townsend & Stockton LLP

(57) ABSTRACT

The invention provides methods and materials for using apatite chromatography supports to dissociate and remove contaminants that are complexed to biological products. The invention further provides materials and methods for dissociating aggregations of target biological molecules or improperly folded target molecules to improve purification of the target molecule.

24 Claims, No Drawings

DISSOCIATION OF PRODUCT-COMPLEXED CONTAMINANTS IN CHROMATOGRAPHY

CROSS-REFERENCE TO RELATED PATENT APPLICATIONS

The present application claims benefit of priority to U.S. Provisional Patent Application No. 61/384,565, filed Sep. 20, 2010, which is incorporated by reference for all purposes.

BACKGROUND OF THE INVENTION

The purification of biological molecules such as antibodies, other therapeutic proteins, virus and virus-like particles, and DNA plasmids for therapeutic or diagnostic purposes is hindered when the biological molecules to be purified are chemically complexed with contaminants. Complexed contaminants decrease the efficiency of the purification process, decrease the reproducibility of the purification process, and affect the stability and pharmacodynamics of the purified biological molecule.

In addition to or in combination with contaminant complexation, biological molecules such as antibodies and therapeutic proteins can also form aggregates. These aggregates render the molecules less biologically active and can increase the immunogenicity of the biological molecule.

BRIEF SUMMARY OF THE INVENTION

The present invention provides methods of purifying a target molecule from a biological sample. In some embodiments, the method comprises:
  (a) contacting the sample comprising the target molecule and complexed contaminants to a metal cation-derivatized apatite solid support or a polycation-derivatized apatite solid support, thereby non-covalently binding the target molecule ("the bound target molecule") to the solid support;
  (b) washing the bound target molecule with an agent(s) that displaces the complexed contaminants from the target molecule under conditions in which the target molecule remains substantially bound to the solid support; and
  (c) eluting the target molecule from the solid support, wherein the eluted target molecule is substantially free of complexed contaminants.

In some embodiments, the method comprises washing the agent(s) from the solid support prior to the eluting step.

In some embodiments, the method comprises converting the metal cation-derivatized apatite solid support or polycation-derivatized apatite solid support to a non-derivatized apatite between the washing step (b) and the eluting step (c) such that the solid support is a non-derivatized apatite solid support during the eluting step (c). In some embodiments, the solid support is a metal cation-derivatized apatite solid support or a polycation-derivatized apatite solid support during the eluting step (c).

In some embodiments, the apatite is hydroxyapatite or fluorapatite. In some embodiments, the apatite is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; hydroxyapatite CHT Type II, 80 micron; fluorapatite CFT Type I, 40 micron; and fluorapatite CFT Type II, 40 micron.

In some embodiments, the target molecule is selected from a protein, antibody, phosphoprotein, virus, virus-like particle, or nucleic acid. In some embodiments, the target molecule is an antibody. In some embodiments, wherein the target molecule is nucleic acid, the nucleic acid is DNA or RNA.

In some embodiments, the complexed contaminants are selected from the group consisting of protein, nucleic acids, lipids, metal ions, sulfides, polysaccharides, and endotoxins.

In some embodiments, the agent is selected from the group consisting of arginine, urea, guanidine, sodium chloride, a salt lacking significant calcium affinity, an organic solvent, a surfactant, and a reducing agent. In some embodiments, the organic solvent is selected from the group consisting of ethylene glycol, propylene glycol, an alcohol, DMSO, and DMF. In some embodiments, the surfactant is selected from the group consisting of a polysorbate (such as polysorbate 20 or polysorbate 80, e.g., Tween-20™ or Tween-80™) surfactant, a nonionic surfactant, a zitterionic surfactant, a Triton surfactant (e.g., octyl phenol ethoxylate (Triton X-100)), a CHAPS surfactant, a CHAPSO surfactant, and octaglucoside. In some embodiments, the reducing agent is selected from the group consisting of a cysteine, dithiothreitol (DTT), dithioerythritol (DTE), or mercaptoethanol.

In some embodiments, the washing step (b) comprises contacting the solid support binding the target molecule with a solution comprising two or more different agents that displace the complexed contaminants. In some embodiments, the two or more different agents comprise:
  i. urea and sodium chloride;
  ii. urea and sodium chloride and cysteine;
  iii. a salt and an organic solvent; or
  iv. a salt and a surfactant.

In some embodiments, the metal cation is selected from the group consisting of magnesium, zinc, iron, calcium, nickel, cobalt, manganese, copper, and chromium. In some embodiments, the metal cation is calcium.

In some embodiments, the complexed contaminants are non-covalently complexed with the target molecule. In some embodiments, the complexed contaminants are covalently complexed with the target molecule. In some embodiments, the complexed contaminants are covalently complexed with the target molecule via a disulfide bond and said agents in the washing step (b) comprise a reducing agent in combination with at least one agent other than a reducing agent, thereby reducing the disulfide bond.

In some embodiments, the target molecule is eluted from the solid support while the complexed contaminants are bound to the solid support. In some embodiments, the target molecule is eluted from the solid support after the complexed contaminants are eluted from the solid support.

In some embodiments, the target molecule is a nucleic acid and the contaminants comprise non-nucleic acid molecules. In some embodiments, the target molecule is a protein and the contaminants comprise non-protein molecules. In some embodiments, the target molecule is a protein and the contaminants comprise a protein other than the target molecule protein. In some embodiments, the target molecule is a virus or virus-like particle and the contaminants comprise non-virus molecules.

The present invention also provides methods of purifying a target molecule from a biological sample comprising an aggregation of contaminants wherein the aggregation of contaminants has different chromatographic retention characteristics as compared to the chromatographic retention characteristics of constituent contaminants that comprise the aggregation. In some embodiments, the method comprises:
  (a) contacting the sample comprising the target molecule and aggregation of contaminants to a metal cation-derivatized apatite solid support or a polycation-derivatized apatite solid support, thereby non-covalently binding the target molecule ("the bound target molecule") to the solid support;

(b) washing the bound target molecule with an agent(s) that dissociates the aggregation of contaminants into the constituent contaminants, wherein the washing is under conditions in which the target molecule remains substantially bound to the solid support; and (c) eluting the target molecule from the solid support, wherein the eluted target molecule is substantially free of the contaminants.

In some embodiments, the method comprises washing the agent(s) from the solid support prior to the eluting step.

In some embodiments, the method comprises converting the metal cation-derivatized apatite solid support or a polycation-derivatized apatite solid support to a non-derivatized apatite between the washing step (b) and the eluting step (c) such that the solid support is a non-derivatized apatite solid support during the eluting step (c). In some embodiments, the solid support is a metal cation-derivatized apatite solid support or a polycation-derivatized apatite solid support during the eluting step (c).

In some embodiments, the apatite is hydroxyapatite or fluorapatite. In some embodiments, the apatite is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; hydroxyapatite CHT Type II, 80 micron; fluorapatite CFT Type I, 40 micron; and fluorapatite CFT Type II, 40 micron.

In some embodiments, the target molecule is selected from a protein, antibody, phosphoprotein, virus, virus-like particle, or nucleic acid. In some embodiments, the target molecule is an antibody. In some embodiments, wherein the target molecule is nucleic acid, the nucleic acid is DNA or RNA.

In some embodiments, the contaminants are selected from the group consisting of protein, nucleic acids, lipids, metal ions, sulfides, polysaccharides, and endotoxins.

In some embodiments, the agent is selected from the group consisting of arginine, urea, guanidine, sodium chloride, a salt lacking significant calcium affinity, an organic solvent, a surfactant, and a reducing agent. In some embodiments, the organic solvent is selected from the group consisting of ethylene glycol, propylene glycol, an alcohol, DMSO, and DMF. In some embodiments, the surfactant is selected from the group consisting of a Tween surfactant, a Triton surfactant, a CHAPS surfactant, a CHAPSO surfactant, and octaglucoside. In some embodiments, the reducing agent is selected from the group consisting of a cysteine, DTT, DTE, or mercaptoethanol.

In some embodiments, the washing step (b) comprises contacting the solid support binding the target molecule with a solution comprising two or more different agents that dissociate the aggregation of contaminants. In some embodiments, the two or more different agents comprise:

i. urea and sodium chloride;
ii. urea and sodium chloride and cysteine;
iii. a salt and an organic solvent; or
iv. a salt and a surfactant.

In some embodiments, the metal cation is selected from the group consisting of magnesium, zinc, iron, calcium, nickel, cobalt, manganese, copper, and chromium. In some embodiments, the metal cation is calcium.

In some embodiments, the aggregation of contaminants is non-covalently complexed with the target molecule. In some embodiments, the aggregation of contaminants is covalently complexed with the target molecule. In some embodiments, the aggregation of contaminants is covalently complexed with the target molecule via a disulfide bond and the washing step comprises a reducing agent in combination with said agent(s), thereby reducing the disulfide bond.

In some embodiments, the target molecule is eluted from the solid support while the contaminants are bound to the solid support. In some embodiments, the target molecule is eluted from the solid support after the contaminants are eluted from the solid support.

In some embodiments, the target molecule is a nucleic acid and the contaminants comprise non-nucleic acid molecules. In some embodiments, the target molecule is a protein and the contaminants comprise non-protein molecules. In some embodiments, the target molecule is a protein and the contaminants comprise a protein other than the target molecule protein. In some embodiments, the target molecule is a virus or virus-like particle and the contaminants comprise non-virus molecules.

The present invention also provides methods of purifying a target molecule monomer from a biological sample comprising target molecule aggregates. In some embodiments, the method comprises:

(a) contacting the sample comprising the target molecule aggregates to a metal cation-derivatized apatite solid support or a polycation-derivatized apatite solid support, thereby non-covalently binding the target molecule aggregates ("the bound target molecule aggregates") to the solid support;

(b) washing the bound target molecule aggregates with an agent(s) that disaggregates the target molecule aggregates under conditions in which the target molecule remains substantially bound to the solid support; and (c) eluting the target molecule as a monomer from the solid support, wherein the eluted target molecule is substantially free of target molecule aggregates.

In some embodiments, the method comprises washing the agent(s) from the solid support prior to the eluting step.

In some embodiments, the method comprises converting the metal cation-derivatized apatite solid support or a polycation-derivatized apatite solid support to a non-derivatized apatite between the washing step (b) and the eluting step (c) such that the solid support is a non-derivatized apatite solid support during the eluting step (c). In some embodiments, the solid support is a metal cation-derivatized apatite solid support or a polycation-derivatized apatite solid support during the eluting step (c).

In some embodiments, the apatite is hydroxyapatite or fluorapatite. In some embodiments, the apatite is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; hydroxyapatite CHT Type II, 80 micron; fluorapatite CFT Type I, 40 micron; and fluorapatite CFT Type II, 40 micron.

In some embodiments, the target molecule is selected from a protein, antibody, phosphoprotein, virus, virus-like particle, or nucleic acid. In some embodiments, the target molecule is an antibody. In some embodiments, wherein the target molecule is nucleic acid, the nucleic acid is DNA or RNA.

In some embodiments, the agent is selected from the group consisting of arginine, urea, guanidine, sodium chloride, a salt lacking significant calcium affinity, an organic solvent, a surfactant, and a reducing agent. In some embodiments, the organic solvent is selected from the group consisting of ethylene glycol, propylene glycol, an alcohol, DMSO, and DMF. In some embodiments, the surfactant is selected from the group consisting of a Tween surfactant, a Triton surfactant, a CHAPS surfactant, a CHAPSO surfactant, and octaglucoside. In some embodiments, the reducing agent is selected from the group consisting of a cysteine, DTT, DTE, or mercaptoethanol.

In some embodiments, the washing step (b) comprises contacting the solid support binding the target molecule with a solution comprising two or more different agents that disaggregate the target molecule aggregates. In some embodiments, the two or more different agents comprise:
  i. urea and sodium chloride;
  ii. urea and sodium chloride and cysteine;
  iii. a salt and an organic solvent; or
  iv. a salt and a surfactant.

In some embodiments, the metal cation is selected from the group consisting of magnesium, zinc, iron, calcium, nickel, cobalt, manganese, copper, and chromium. In some embodiments, the metal cation is calcium.

In some embodiments, wherein the target molecule aggregates are stabilized by non-covalent interactions. In some embodiments, wherein the target molecule aggregates are stabilized by covalent interactions. In some embodiments, the target molecule aggregates are homomeric covalent aggregates. In some embodiments, the target molecule aggregates are heteromeric covalent aggregates. In some embodiments, the target molecule aggregates are stabilized by covalent interactions via a disulfide bond and the washing step comprises a reducing agent in combination with said agent(s), thereby reducing the disulfide bond.

The present invention further provides methods of intramolecular disulfide remodeling and purifying a target molecule having proper disulfide bonding from a biological sample. In some embodiments, the method comprises:
  (a) contacting the sample comprising the target molecule having improper disulfide bonding to a metal cation-derivatized apatite solid support or a polycation-derivatized apatite solid support, thereby non-covalently binding the target molecule having improper disulfide bonding ("the bound target molecule") to the solid support;
  (b) washing the bound target molecule with a reducing agent in combination with at least one more agent under conditions that reduce disulfide bonds in the bound target molecule, wherein the target molecule remains substantially bound to the solid support;
  (c) subjecting the target molecule to conditions allowing the target molecule to refold to have proper disulfide bonding; and
  (d) eluting the target molecule having proper disulfide bonding from the solid support, wherein the eluted target molecule having proper disulfide bonding is substantially free of target molecule having improper disulfide bonding.

In some embodiments, the method comprises washing the reducing agent and the at least one more agent from the solid support prior to the eluting step.

In some embodiments, the method comprises converting the metal cation-derivatized apatite solid support or a polycation-derivatized apatite solid support to a non-derivatized apatite between the washing step (b) and the eluting step (c) such that the solid support is a non-derivatized apatite solid support during the eluting step (c). In some embodiments, the solid support is a metal cation-derivatized apatite solid support or a polycation-derivatized apatite solid support during the eluting step (c).

In some embodiments, the apatite is hydroxyapatite or fluorapatite. In some embodiments, the apatite is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; hydroxyapatite CHT Type II, 80 micron; fluorapatite CFT Type I, 40 micron; and fluorapatite CFT Type II, 40 micron.

In some embodiments, the target molecule is selected from a protein, antibody, phosphoprotein, virus, virus-like particle, or nucleic acid. In some embodiments, the target molecule is an antibody.

In some embodiments, the reducing agent is selected from the group consisting of a cysteine, DTT, DTE, or mercaptoethanol. In some embodiments, the at least one more agent is selected from the group consisting of arginine, urea, guanidine, sodium chloride, a salt lacking significant calcium affinity, an organic solvent, and a surfactant. In some embodiments, the organic solvent is selected from the group consisting of ethylene glycol, propylene glycol, an alcohol, DMSO, and DMF. In some embodiments, the surfactant is selected from the group consisting of a Tween surfactant, a Triton surfactant, a CHAPS surfactant, a CHAPSO surfactant, and octaglucoside.

In some embodiments, the washing step (b) comprises contacting the solid support binding the target molecule with a solution comprising the reducing agent in combination with at least two more agents. In some embodiments, the at least two more agents comprise:
  i. urea and sodium chloride;
  ii. a salt and an organic solvent; or
  iii. a salt and a surfactant.

In some embodiments, the metal cation is selected from the group consisting of magnesium, zinc, iron, calcium, nickel, cobalt, manganese, copper, and chromium. In some embodiments, the metal cation is calcium.

DEFINITIONS

Terms are defined so that the invention may be understood more readily. Additional definitions are set forth throughout the detailed description.

"Apatite solid support" refers to a mineral of calcium and phosphate in a physical form suitable for the performance of chromatography. Examples include but are not limited to hydroxyapatite and fluorapatite. This definition is understood to include the native as well as metal cation-derivatized and polycation-derivatized forms of an apatite solid support.

"Metal-derivatized apatite solid support" refers to an apatite solid support that has been treated with a divalent metal cation in the absence of phosphate buffer, to create a surface in which the negatively charged native apatite phosphate groups are neutralized by binding metal ions, and the metal ions are available to participate in coordination interactions with biomolecules such as proteins, polynucleotides, and viruses. One example includes apatites that are derivatized with calcium. This leaves a surface with the native calcium residues and the secondary calcium residues. Apatites derivatized with other metals would leave a surface of mixed metal character: the original calcium plus the derivatizing metal or metals.

"Cationic polymer-modified apatite support," also referred to as a "polycation derivatized apatite support," refers to an apatite solid support that has been treated with a positively charged polymer to create a surface in which the negatively charged native apatite phosphate groups are neutralized and excess positively charged groups on the polymer impart a net electropositive charge on the surface as a whole. Polycations, or "cationic polymers", refer to molecules containing three or more positive charges, and in some embodiments, comprise 4 or more, 5 or more, 6 or more, 7 or more, 8 or more, or 9 or more positive charges within a single molecule. Polyethyleneimine is an example of a cationic polymer that can be used for this purpose. The polymer may range in size from a few hundred to more than 100,000 daltons. Other cationic polymers that may be used to product a similar effect include but are not limited to polylysine, polyarginine, and polyallylamine.

The terms "decomplexing agent" or "decomplexant" refer to a compound that dissociates, displaces, or disaggregates a target molecule of interest from a complex or aggregation, for example from a target molecule-contaminant complex, a complex with improperly matched or unmatched disulfide bonds or unstable trisulfides, or a multimeric target molecule aggregate. Exemplary agents include, but are not limited to, arginine, urea, guanidine, sodium chloride, salts lacking significant calcium affinity, organic solvents, surfactants, and reducing agents.

"Target molecule" refers to a biomolecule, or molecule of biological origin, for purification according to the methods of the present invention. Target molecules include, but are not limited to, proteins, polynucleotides, viruses, and virus-like particles. Examples of proteins include but are not limited to antibodies, enzymes, growth regulators, clotting factors, and phosphoproteins. Examples of polynucleotides include DNA and RNA. Examples of viruses include enveloped and non-enveloped viruses.

"Antibody" refers to any immunoglobulin or composite form thereof. The term may include, but is not limited to, polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

"Contaminant" or "complexed contaminant" refers to an unwanted constituent that is associated with a target molecule to be purified. The association may be either covalent or non-covalent without respect to the mechanism of association. Examples of contaminants include, but are not limited to, proteins, nucleic acids, lipids, various cell culture media components and additives, metal ions, thioredoxins, sulfides, polysaccharides, and endotoxins.

"Aggregate" refers to an association of at least two target molecules, e.g., antibodies, and often more (e.g., 5, 10, 20 or more target molecules). The association may be either covalent or non-covalent without respect to the mechanism by which the target molecules are associated. The association may be direct between the target molecules or indirect through other molecules that link the target molecules together. Examples of the latter include but are not limited to disulfide linkages via proteins, hydrophobic associations via lipids, charge associations via DNA, affinity associations via leached protein A, or mixed mode associations via multiple components. As used herein, the term encompasses both "homomeric" aggregates (associations of multimers (dimers, trimers, tetramers, etc.) of a single molecule of interest) and "heteromeric" aggregates (associations of target molecules, e.g., proteins, with other non-target molecules, e.g., non-target proteins).

"Biological product preparation" refers to any composition containing a target molecule to be purified. In some embodiments, the target molecule to be purified is an antibody.

"Preparative applications" refers to situations in which the invention is practiced for the purpose of obtaining a purified biological product (e.g., antibody or other protein) for research, diagnostic, therapeutic, or other applications. Such applications may be practiced at any scale, ranging from milligrams to kilograms of biological product per batch.

DETAILED DESCRIPTION OF THE INVENTION

I. Introduction

Methods are provided for using apatite chromatography supports for the dissociation and removal of contaminants that are chemically complexed to target biological molecules in biological product preparations. The methods of the present invention are useful for removing complexed contaminants as well as heterogeneous "supercontaminants," or aggregations of contaminants with different chromatographic retention characteristics than the chromatographic retention characteristics of constituent contaminants that comprise the aggregation, thereby increasing the degree of purification of the target molecule.

The present invention also provides methods for using apatite chromatography supports to dissociate aggregates of target molecules into monomers of the target molecule. The dissociation of target molecule aggregates reduces the aggregate content of the biological product preparation, for example in antibody preparations or therapeutic protein preparations. The benefits of reducing aggregates in a biological product preparation include, for example, a reduction in patient risk associated with administering therapeutic proteins; improved performance of immunodiagnostic reagents; and potentially increased recovery of native target product by restoring the target product to its native form rather than "removing" aggregates.

The present invention further provides methods for using apatite chromatography supports to restore a target molecule to its native characteristics. In some embodiments, the methods of the present invention dissociate improper disulfide bonding in the biological product preparation and enhance the ability of the target molecule to refold to have proper disulfide bonding. Restoring the target molecule to its native characteristics enables more effective purification and higher recovery of the target molecule.

II. Apatite Chromatography

The present invention provides for purifying a target molecule from a biological sample using an apatite solid support in combination with a decomplexing agent. The apatite chromatography support also provides a decomplexing function and helps to achieve a higher degree of complex dissociation and contaminant removal than can be achieved in comparison to the use of the same decomplexing agents as described herein in the absence of an apatite chromatography support.

Various apatite solid supports are available commercially, any of which can be used in the practice of this invention. These include but are not limited to hydroxyapatite and fluorapatite. Commercially available examples include but are not limited to ceramic hydroxyapatite (CHT) or ceramic fluorapatite (CFT). In some embodiments, the apatite solid support is a column.

"Hydroxyapatite" refers to a chromatography support comprising an insoluble hydroxylated mineral of calcium phosphate with the structural formula $Ca_{10}(PO_4)_6(OH)_2$. Its dominant modes of interaction are phosphoryl cation exchange and calcium metal affinity.

"Fluorapatite" refers to a chromatography support comprising an insoluble fluoridated mineral of calcium phosphate with the structural formula $Ca_{10}(PO_4)_6F_2$. Its dominant modes of interaction are phosphoryl cation exchange and calcium metal affinity.

"Ceramic" hydroxyapatite (CHT) or "ceramic" fluorapatite (CFT) refer to forms of the respective minerals in which nanocrystals are agglomerated into particles and fused at high temperature to create stable ceramic microspheres suitable for chromatography applications. Commercial examples of ceramic hydroxyapatite include, but are not limited to, CHT Type I and CHT Type II. Commercial examples of fluorapatite include, but are not limited to, CFT Type I and CFT Type II. Unless specified, CHT and CFT refer to roughly spherical particles of any average diameter, including but not limited to about 10, 20, 40, and 80 microns. The choice of hydroxyapatite or fluorapatite, the type, and average particle diameter can be determined by the skilled artisan.

In some embodiments, the apatite is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; hydroxyapatite CHT Type II, 80 micron; fluorapatite CFT Type I, 40 micron; and fluorapatite CFT Type II, 40 micron.

In some embodiments, CHT or CFT is packed in a column. In some embodiments, CHT or CFT is packed in a column of about 5 mm internal diameter and a height of about 50 mm, for evaluating the effects of various agents and combinations of agents on the dissociation of target molecule aggregates and/or target molecule-contaminant complexes and elution characteristics of target molecules from a biological product preparation. In some embodiments, CHT or CFT is packed in a column of any dimensions required to support preparative applications. Column diameter may range from 1 cm to more than 1 meter, and column height may range from 5 cm to more than 30 cm depending on the requirements of a particular application. Appropriate column dimensions can be determined by the skilled artisan.

Metal Cation-Derivatized Apatites

In some embodiments, the native hydroxyapatite and/or fluorapatite is converted to a metal cation-derivatized form by exposure to soluble metal cation in the absence of phosphate, thereby altering the selectivity of the apatite support. Examples of metal cations suitable for derivatization of native apatites include, but are not limited to, magnesium, zinc, iron, calcium, nickel, cobalt, manganese, copper, and chromium.

In some embodiments, the derivatized apatite is a calcium-derivatized apatite. Calcium derivatization largely eliminates apatite phosphate groups, replacing them with secondary calcium groups. Calcium derivatization increases the affinity of the apatite for phosphorylated molecules, thereby increasing the complex-dissociative potential of the support and increasing the effective purification of the target molecule of interest.

Methods of converting native apatite to a metal cation (e.g., calcium)-derivatized form are known in the art and are described, for example, in US 2009/0187005 and US 2009/0186396, each of which is incorporated by reference herein in its entirety. Briefly, in some embodiments, an apatite solid support is equilibrated with a solution comprising a calcium salt at a concentration of about 2-5 mM, in the presence of one or more buffering compounds to confer adequate pH control. In some embodiments, the calcium salt is present at a concentration of about 1 mM to about 100 mM, about 1 mM to about 50 mM, about 1 mM to about 20 mM, or about 2 mM to about 10 mM. Buffering compounds may include but are not limited to MES, HEPES, BICINE, imidazole, and Tris. In some embodiments, the apatite is calcium-derivatized by applying to the apatite support a buffer comprising about 20 mM HEPES, about 20 mM MES, and about 5 mM calcium at about pH 7.

An apatite chromatography support of the present invention may be eluted in its metal cation (e.g., calcium)-derivatized form, or alternatively may be restored to its native (i.e., non-derivatized) form prior to elution. In some embodiments, metal cation-derivatized apatites are restored to their native forms by exposure to phosphate buffer, at which point they may be eluted by methods commonly applied for elution of native apatite supports. For example, calcium-derivatized apatite can be restored to native apatite upon washing with phosphate buffer. For some metal cation-derivatized apatites, the derivatization is only partially reversible or is irreversible. In some embodiments, the derivatized apatite (e.g., a calcium-derivatized apatite) is restored to its native condition by applying to the apatite support a buffer comprising about 10 mM phosphate.

Polycation Cation-Derivatized Apatites

In some embodiments, the native hydroxyapatite and/or fluorapatite is converted to a polycation-derivatized form by exposure to a soluble polycation in the absence of phosphate, thereby altering the selectivity of the apatite support. Examples of polycations suitable for derivatization of native apatites include, but are not limited to, polyethyleneimine (PEI), and polyamines such as polyethanolamine, polylysine, polyarginine, and polyallylamine.

In some embodiments, the native hydroxyapatite is converted to a metal cation-derivatized apatite prior to being converted to a polycation-derviatized form. This conversion permits proteins that would otherwise be eluted by high salt washes from native or polycation-derivatized apatite to remain bound to the support. It also replaces the native phosphoryl cation exchange reactivity with a polycation-based anion exchange function that enhances binding of acidic contaminants such as DNA, endotoxin, virus, leached protein A, and host cell proteins.

Derivitization of apatite supports can generally involve simply contacting the support with a solution containing a sufficient amount of the polycation at a pH in which the polycation is sufficiently cationic to bind to the apatite support. For example, in some embodiments, PEI or another polycation is titrated to a pH of about 6.5-7.0 and diluted, optionally ins a buffer such as 50 mM Hepes, to a concentration of 0.1%-2%. In some embodiments, the solid support is subsequently washed with a buffer (e.g., 50 mM Hepes, pH 7.0), followed by equilibration with 10 mM phosphate.

The concentration of polycation should be sufficient to block a sufficient amount of negative charges on the apatite phosphates such that cationic virucidal agent do not significantly bind to the polycation-derivatized apatite. Successful derivatization can be confirmed, for example, by applying a sample of DNA (e.g., 0.1 mg/mL salmon sperm DNA in 50 mM Hepes, pH 7.0) and comparing the phosphate concentration at which the DNA elutes in a phosphate gradient, to the eluting phosphate concentration in a native (not derivatized) apatite support column. DNA mostly elutes at about 250-300 mM phosphate from native CHT, but mostly not until 300-500 mM form polycation modified apatite. Cellular protein in typical biological samples, while containing some polycationic polypeptides, is not sufficient to block a sufficient amount of apatite phosphates for the purposes described herein.

The derivatization solution will generally include a buffering compound to confer adequate pH control. Ideally, the buffer will be positively charged or zwitterionic at the pH used (e.g., about pH 6-7.5, or, e.g., about 6.5-7.0) to avoid possible interactions of the buffer and the polycation. Buffering compounds may include but are not limited to MES, HEPES, histidine, histamine, and and imidazole.

III. Target Molecules

The present invention provides methods of purifying a target molecule from a biological sample. In some embodiments, the target molecule in the biological sample is complexed with one or more contaminants or an aggregation of contaminants. In some embodiments, the target molecule in the biological sample is an aggregation of target molecules. In some embodiments, the target molecule in the biological sample exists in a form in which the target molecule has improper disulfide bonding and/or is improperly folded.

Target molecules of the present invention include any biological molecule that may be purified using apatite chromatography. Examples of target molecules include, but are not limited to, proteins (e.g., antibodies, enzymes, growth regulators, clotting factors, and phosphoproteins), polynucleotides (e.g., DNA and RNA), viruses, and virus-like particles.

In some embodiments, the target molecule is an antibody or antibody fragment. Antibody preparations for use in the present invention can include unpurified or partially purified antibodies from natural, synthetic, or recombinant sources. Unpurified antibody preparations may come from various sources including, but not limited to, plasma, serum, ascites fluid, milk, plant extracts, bacterial lysates, yeast lysates, or conditioned cell culture media. Partially purified preparations may come from unpurified preparations that have been processed by at least one chromatography, precipitation, other fractionation step, or any combination of the foregoing. The chromatography step or steps may employ any method, including but not limited to size exclusion, affinity, anion exchange, cation exchange, protein A affinity, hydrophobic interaction, immobilized metal affinity chromatography, or mixed-mode chromatography. The precipitation step or steps may include salt or PEG precipitation, or precipitation with organic acids, organic bases, or other agents. Other fractionation steps may include but are not limited to crystallization, liquid:liquid partitioning, or membrane filtration.

IV. Contaminants and Aggregations

In some embodiments, the methods of the present invention are useful for decomplexing one or more contaminants that are complexed with a target molecule in order to enhance the purification of the target molecule. Examples of contaminants include, but are not limited to, proteins, nucleic acids, lipids, various cell culture media components and additives, metal ions, polysaccharides, endotoxins, thioredoxins, and sulfides (e.g., sulfides created by cells during cell culturing that can lead to the insertion of a sulfur atom into a disulfide bond of the target molecule and resulting in an unstable trisulfide, e.g., during the production of IgG monoclonal antibodies in mammalian cell culture).

Target molecule-contaminant complexes may be formed and/or stabilized by any of various chemical interactions or combinations of chemical interactions. The chemical interactions may be covalent or non-covalent. Examples of chemical interactions between target molecules and contaminants include, but are not limited to, electrostatic interactions, hydrogen bonding, hydrophobic interactions, metal affinity interactions, pi-pi bonding, pi-cation interactions, and redox reactions. In some embodiments, the complexed contaminants are covalently complexed with the target molecule via a disulfide bond.

In some embodiments, the target molecule is complexed with heterogeneous aggregations of contaminants, or "super-contaminants," having different chromatographic retention characteristics as compared to the chromatographic retention characteristics of constituent contaminants that comprise the aggregation of contaminants. The methods of the present invention can be used to dissociate the aggregation of contaminants into the constituent contaminants. As described herein, the dissociation of aggregations of contaminants into constituent contaminants, which have more homogenous and narrowly defined chromatographic retention characteristics, aids in the removal of the contaminants and increases the target molecule purification potential and reproducibility of purification processes.

In some embodiments, the target molecule is a protein and the contaminants comprise non-protein molecules (e.g., a nucleic acid). In some embodiments, the target molecule is a protein and the contaminants comprise a protein other than the target molecule protein. In some embodiments, the target molecule is a nucleic acid and the contaminants comprise non-nucleic acid molecules. In some embodiments, the target molecule is a virus or a virus-like particle and the contaminants comprise non-virus molecules.

The present invention also provides methods of disaggregating target molecule aggregates. In some embodiments, the target molecule aggregates are homomeric aggregates, comprising only the target molecule of interest, in which the target molecules form multimers (e.g., a multimer of IgG). Homomeric aggregates can be stabilized by covalent interactions or by non-covalent interactions. In some embodiments, the homomeric target molecule aggregates are stabilized by disulfide bonds.

In some embodiments, the target molecule aggregates are heteromeric aggregates, comprising a target molecule of interest as well as one or more types of molecules other than the target molecule (e.g., a IgG of interest aggregated with one or more non-IgG proteins). Heteromeric aggregates can be stabilized by covalent intereactions or by non-covalent interactions. In some embodiments, the heteromeric target molecule aggregates are stabilized by disulfide bonds.

V. Methods

The methods of the present invention use apatite chromatography to purify a target molecule from a biological sample. Generally, the methods of the present invention involve contacting the sample comprising the target molecule to a metal-derivatized apatite solid support or a polycation-derivatized apatite solid support, thereby non-covalently binding the target molecule to the apatite support; washing the bound target molecule with one or more agents as described herein, wherein the target molecule remains substantially bound to the apatite support; and eluting the target molecule from the apatite support.

In some embodiments, the target molecule to be purified is complexed to one or more contaminants, and the methods comprise contacting the target molecule-contaminant complex with one or more agents that displace the complexed contaminants from the target molecule and eluting the target molecule from the apatite, wherein the eluted target molecule is substantially free of the complexed contaminants.

In some embodiments, the target molecule to be purified is complexed to an aggregation of contaminants, and the methods comprise contacting the target molecule-contaminant complex with one or more agents that dissociate the aggregation of contaminants from the target molecule and eluting the target molecule from the apatite, wherein the eluted target molecule is substantially free of the contaminants.

In some embodiments, the target molecule to be purified is an aggregate of target molecules, and the methods comprise contacting the target molecule aggregates with one or more agents that disaggregate the target molecule aggregates and eluting the target molecule as a monomer from the apatite, wherein the eluted target molecule is substantially free of target molecule aggregates.

In some embodiments, the target molecule to be purified has improper disulfide bonding, and the methods comprise contacting the target molecule having improper disulfide bonding with a reducing agent in combination with at least one more agent under conditions that reduce the disulfide bonds, subjecting the target molecule to conditions allowing the target molecule to refold to have proper disulfide bonding, and eluting the target molecule having proper disulfide bonding from the apatite, wherein the eluted target molecule is substantially free of target molecules having improper disulfide bonding.

Contacting Step

In preparation for contacting the sample comprising the target molecule with the apatite support (e.g., apatite column), it is usually necessary to equilibrate the chemical environment inside the column. This is accomplished by flowing an equilibration buffer through the column to establish the appropriate pH, conductivity, concentration of salts, and/or the identity, molecular weight, and, if included, concentration of nonionic organic polymer.

The equilibration buffer can include calcium or other metal salts as appropriate, but generally will not include phosphate or other salts that remove the metal (e.g., calcium) ion derivitization from the apatite. In some embodiments the calcium salts are at a concentration of about 2-5 mM. It may optionally include a nonionic organic polymer (e.g., polyethylene glycol or other nonionic organic polymer described in US Patent Publication No. 2008/0177048) at a concentration of about 0.01-50%, and/or a buffering compound to confer adequate pH control. Buffering compounds may include but are not limited to MES, HEPES, BICINE, imidazole, and Tris. The pH of the equilibration buffer for hydroxyapatite can range from about pH 6.5 to pH 9.0. The pH of the equilibration buffer for fluorapatite can range from about pH 5.0 to 9.0.

In some embodiments, the apatite column is metal cation-derivatized with a solution comprising a metal cation salt at a concentration of about 2-5 mM, in the presence of one or more buffering compounds to confer adequate pH control. In some embodiments, the apatite column is calcium-derivatized by applying an equilibration buffer comprising 5 mM calcium salt in the presence of 20 mM HEPES and 20 mM MES and having a pH of about 7.

The sample comprising the target molecule, interchangeably referred to herein as the biological product preparation, can also be equilibrated to conditions compatible with the column equilibration buffer before the invention is practiced. This consists of adjusting the pH, concentration of salts, and other compounds. In some embodiments, the sample is equilibrated by adding calcium chloride to the sample to a final calcium concentration of 5 mM.

After the column and biological product preparation have been equilibrated, the biological product preparation may be contacted with the column. The preparation may be applied at a linear flow velocity in the range of, but not limited to, about 50-600 cm/hr. Appropriate flow velocity can be determined by the skilled artisan.

In some embodiments, contacting the apatite solid support with a sample comprising a target molecule (which may be complexed with contaminants or aggregations of contaminants, aggregated target molecule, and/or target molecule having improper disulfide bonding) non-covalently binds the target molecule to the solid support.

Washing Step

Following binding of the target molecule to the apatite solid support, the bound target molecule is washed with one or more agents that displace the complexed contaminants from the target molecule or the improper disulfide bonds of the target molecule, dissociate the aggregation of contaminants from the target molecule, or disaggregate the target molecule aggregates, under conditions in which the target molecule remains substantially bound to the solid support. Without intending to limit the scope of the invention, it is believed that the agent(s) decomplex the target molecule from the contaminants or aggregations by weakening the association (i.e., covalent interaction or non-covalent interaction) between them. The decomplexing agent(s) act in combination with the apatite solid support, which itself functions to dissociate or displace contaminants or aggregations from the target molecule. In some cases, for example when the target molecule has improper disulfide bonding or when the target molecule aggregate or target molecule-contaminant complex is stabilized by disulfide bonds, the decomplexing agent(s) may relax the structure of the target molecule, allow improper and/or unnatural disulfide bonds to be displaced more easily, and enhance the ability of the target molecule to self-restore proper natural disulfide bonding.

A variety of agents can be used to displace, dissociate, or disaggregate the contaminants, improper disulfide bonds, or aggregates. Typically, the agent is a compound that does not substantially interfere with the binding of the target molecule to the apatite column (e.g., for a calcium-derivatized apatite column, the agent is one that lacks significant affinity for calcium). In some embodiments, the agent is a liquid. In some embodiments, the agent is a compound that is dissolved in liquid.

In some embodiments, the agent is selected from the group consisting of arginine, urea, guanidine, sodium chloride, a salt lacking significant calcium affinity (e.g., NaCl, KCl, sodium acetate, potassium acetate, sodium perchlorate, potassium perchlorate, guanidinium salts, amino acid salts, and thiocyanates), an organic solvent, a surfactant, and a reducing agent. In some embodiments, the agent is urea. In some embodiments, the agent is sodium chloride.

Exemplary concentrations of exemplary agents include, but are not limited to, the following:

Sodium chloride: 0.1 to 5 M, e.g., 0.5-2.0 M.

Arginine: 0.05-1.00 M, e.g., 200-600 mM.

KCl: same as NaCl

Guanidine: for most cases (e.g., for IgG purification) 100 mM-1 M, but in more difficult cases up to 2 M. In situations where protein unfolding is not a concern, up to 6M.

Perchlorate: 100 mM to 1 M, up to saturation in extreme cases.

Thiocyante: 100 mM to 1 M, up to saturation in extreme cases.

Urea: 1-2 M. Secondary range 200 mM to 4 M. Can be used up to 10 M in extreme cases.

Organic solvent: ethanol, isopropanol, phenoxyethanol, Dimethylsulfoxide (DMSO) 1-50%, e.g., 2-20%. DMF lower: 0.1-10%, e.g., 0.1-1%.

Ethylene glycol or propylene glycol: 5-50%, e.g., 15-25.

Surfactants: generally less than their critical micelle conentrations, which vary considerably. In some embodiments, with tweens/triton/polysorbates, less than 0.01%, with CHAPS, CHAPSO, up to, e.g., 0.1%.

Reducing agents: DTT, mercaptoethanol, cysteine: 1-50 mM, e.g., 5-25 mM.

In some embodiments, the agent is an organic solvent. Exemplary organic solvents include, but are not limited to, ethylene glycols, propylene glycols, alcohols, DMSO, and DMF.

In some embodiments, the agent is a surfactant. Exemplary surfactants include, but are not limited to, polysorbate (such as polysorbate 20 or polysorbate 80, e.g., Tween-20™ or Tween-80™) surfactant, a nonionic surfactant, a zitterionic surfactant, a Triton surfactant (e.g., octyl phenol ethoxylate (Triton X-100)), a CHAPS surfactant, a CHAPSO surfactant, and octaglucoside In some embodiments, the agent is a reducing agent. Exemplary reducing agents include, but are not limited to, cysteine, dithiothreitol ("DTT"), dithioerythreitol ("DTE"), mercaptoethanol ("BME"), 2-mercaptoethylamine-HCl ("2-MEA"), glutathione ("GSH"), or tris(2-carboxyethyl)phosphine ("TCEP").

In some embodiments, the washing step comprises contacting the solid support binding the target molecule with one decomplexing agent. In some embodiments, the washing step comprises contacting the solid support binding the target molecule with two, three, four, or more different decomplexing agents. In some embodiments, the washing step comprises contacting the solid support binding the target molecule with a solution comprising the two or more different agents. As shown in the Examples section below, the use of a solution comprising at least two decomplexing agents may increase the effectiveness of dissociating a complexed contaminant or aggregation of contaminants from a target molecule, or of disaggregating a target molecule aggregate into target molecule monomers, as compared to the use of each decomplexing agent alone.

In some embodiments, the two or more different decomplexing agents comprise: urea and sodium chloride; urea, sodium chloride, and a reducing agent; a salt and an organic solvent; or a salt and a surfactant.

As a non-limiting example, the methods of the present invention are useful for displacing contaminating metal ions from a target molecule. Metal ions can form stable complexes with target molecules (e.g., proteins), altering the characteristics of the target molecule (e.g., altering charge, hydrophobicity, stability, function, and antigenicity). Additionally, metal ions can form bridged complexes between the target molecule and other contaminants (e.g., between a target protein and a contaminant DNA) which are highly stable and resistant to salts, even at high concentrations, thus making the metal bridged complexes resistant to typical non-apatite purification methods. Although it is known that purification with an apatite solid support, including a calcium-derivatized apatite support, is able to remove metal ions that can form metal-bridged complexes, the use of an apatite solid support in combination with a solution comprising one or more decomplexing agents as described herein enhances the dissociation of metal-bridged complexes by dissociating not only metal affinity interactions, but also other interactions that stabilize the target molecule-contaminant complex (e.g., electrostatic interactions, hydrogen bonds, and/or hydrophobic interactions).

In some embodiments, a solution comprising a reducing agent in combination with at least one more decomplexing agent may be useful in dissociating disulfide bonds, e.g., where there is improper disulfide bonding, or in decomplexing an extra sulfide. In some embodiments, the solution comprises a reducing agent in combination with at least one more decomplexing agent.

As a non-limiting example, a solution comprising a reducing agent is useful for displacing a sulfide contaminant that is complexed with a target molecule, e.g., a sulfide that is derived from $H_2S$ gas produced by cell cultures and that inserts itself into pre-existing disulfide bonds of the target molecule to create unstable trisulfide. A solution comprising the reducing agent (e.g., cysteine) is contacted to the bound target molecule on the apatite solid support under conditions that decomplex the extra sulfide, thus dissociating the sulfide contaminant from the target molecule. In some embodiments, the solution comprising the reducing agent further comprises at least one more decomplexing agent (e.g., sodium chloride and/or urea). The use of a reducing agent in combination with at least one other agent may increase the efficiency of the decomplexation and repair of the target molecule and provides the additional benefit of removing other contaminants that may be complexed to the target molecule. The target molecule is subsequently eluted as described below.

As another non-limiting example, a solution comprising a reducing agent is useful for decomplexing a target molecule aggregate that is stabilized by disulfide bonds (e.g., from a free sulfo group of one target molecule monomer forming a stable disulfide bond with a free sulfo group of another target molecule monomer). A solution comprising the reducing agent (e.g., cysteine), or a solution comprising the reducing agent in combination with at least one more decomplexing agent (e.g., sodium chloride and/or urea) is contacted to the bound target molecule aggregate on the apatite solid support under conditions that dissociates the disulfide bonds, thus decomplexing the aggregate into monomers of the target molecule. The target molecule monomers are subsequently eluted as described below.

As yet another non-limiting example, a solution comprising a reducing agent is useful for remodeling a target molecule having improper disulfide bonding (e.g., a naturally occurring mixed disulfide variant of IgG) into a target molecule that is substantially free of improper disulfide bonding. A solution comprising the reducing agent (e.g., cysteine), or a solution comprising the reducing agent in combination with at least one more decomplexing agent (e.g., sodium chloride and/or urea) is contacted to the bound target molecule on the apatite solid support under conditions that reduce disulfide bonds in the target molecule. The target molecule is subjected to conditions allowing the target molecule to refold to have proper disulfide bonding, and is subsequently eluted as described below. In some embodiments, the conditions that allow the target molecule to refold to have proper disulfide bonding may be achieved by varying the amount of reducing agent and/or at least one more decomplexing agent that is present in the solution, e.g., by washing the bound target molecule with a solution that does not comprise a reducing agent.

In some embodiments, the decomplexing agent or agents are removed from the solid support prior to eluting the target molecule from the solid support. The agent or agents can be removed from the solid support, e.g., by washing the solid support with any suitable buffer.

In some embodiments, the decomplexing agent or agents are not removed from the solid support prior to eluting the target molecule from the solid support.

Eluting Step

Following the wash step, the target molecule is eluted from the apatite solid support. In some embodiments, the apatite solid support from which the target molecule is eluted is converted from a metal cation (e.g., calcium)-derivatized form to a non-derivatized form after the washing step but prior to elution of the target molecule. The metal cation-derivatized apatite solid support can be converted to a non-derivatized form by contacting the apatite solid support with a phosphate buffer. In some embodiments, the derivatized apatite is converted to a non-derivatized condition by contacting the apatite solid support with a buffer comprising about 10 mM phosphate at about pH 7.

In some embodiments, the apatite solid support from which the target molecule is eluted remains in a metal cation (e.g., calcium)-derivatized form during the elution of the target molecule.

Elution conditions can comprise, for example, increasing the concentration of ion and/or buffer, thereby competing the target molecule from the support. For example, in some embodiments, the target molecule is eluted with a sodium chloride gradient in which the buffer concentration is raised to, e.g., at least 250 mM, e.g., 250 mM-1.5 M, e.g., 500 mM-1.0 M. Optionally, the pH is maintained between pH 5.0-10.0, e.g., 5.5-8.5, e.g., between pH 6.5-7.5. Elution gradients can be linear or discontinuous.

In some embodiments, the target molecule is eluted with a linear gradient to about 1 M NaCl at about 10 mM phosphate and at a pH of about 7.

Optionally, further salt (e.g., such as the salt used in the washing step) is not included in the elution buffer.

In some embodiments, the target molecule is eluted from the solid support while the contaminants from which the target molecule was dissociated or disaggregated are bound to the solid support. In some embodiments, the target molecule is eluted from the solid support after the contaminants from which the target molecule was dissociated or disaggregated are eluted from the solid support.

In some embodiments, at least 50%, 60%, 70%, 80%, 90%, 95%, or more of the target molecule bound to the solid support is eluted in the elution step.

In some embodiments, the methods of the present invention increase removal of complexed contaminants from the target molecule by at least 2-fold, e.g., at least 3-fold, at least 4-, 5-, 10-, 20-, 30-, 40-, 50-, 100-fold or more as compared to methods of target molecule purification not comprising the apatite chromatography and decomplexing agents of the present invention.

In some embodiments, the target molecule that is eluted from the solid support is substantially free of contaminants. As used herein, "substantially free" means that the contaminants are 10% or less of the purified target molecule, e.g., less than 10%, 5%, 4%, 3%, 2%, 1%, 0.1%, 0.001%, or completely free of contaminants.

Whether complexed contaminants have been dissociated from the target molecule, and the extent to which complexed contaminants have been dissociated from the target molecule, can be determined by generating elution profiles for the chromatography run and looking at the pattern and/or size of peaks produced during the purification process. Additionally, when the target molecule or contaminant is DNA or protein, the removal of contaminants from the target molecule can be evaluated by measuring the A260 (absorbance at 260 nm; DNA) and/or A280 (absorbance at 280 nm; protein) profiles.

For example, elution profiles were generated for the Examples described herein. The absence or presence of DNA contaminants with IgG target molecule was evaluated based on the peak patterns for the purification runs and by measuring the A254 (DNA) and A280 (IgG) profiles. For Examples 2-4 (IgG purification in the presence of urea wash, a sodium chloride wash, and a urea+sodium chloride wash, respectively), elution profiles were generated and compared to Example 1 (negative control; IgG purification in the absence of a decomplexing agent). Contaminant decomplexation from the target molecule was revealed by the relatively smaller and more narrowly defined contaminant elution peaks before antibody elution. Contaminant decomplexation from the target molecule was also revealed by the increase in DNA in the post-elution phosphate cleaning step.

In some embodiments, at least some contaminants (e.g., nucleic acids, such as DNA) remain linked to the solid support following elution of the target molecule.

EXAMPLES

The following examples are offered to illustrate, but not to limit the claimed invention.

The following examples describes removal of complexed DNA from monoclonal IgG. IgGs mostly elute from apatites at high NaCl concentrations in the presence of low phosphate concentrations, thereby limiting, though not preventing removal of complexed DNA from antibodies. The use of calcium-derivatized apatite permits IgG retention to be conserved at high NaCl concentrations, allowing the use of NaCl to remove DNA while retaining antibodies. Other salts without significant calcium affinity can likewise be used without limitation, potentially including but not limited to chaotropic salts such as guanidine, perchlorates, and thiocyanates.

Example 1

CHT type I 40 micron was equilibrated with 20 mM Hepes, 20 mM MES, 5 mM calcium chloride, pH 7. Calcium chloride was added to cation exchange purified IgG, to a final calcium concentration of 5 mM, and the IgG was loaded onto the CHT column. As a control, a reference run was conducted in which the column was washed with 10 mM phosphate to restore the apatite support to its native (non-calcium dervatized) form prior to elution with a 20 CV linear sodium chloride gradient at 10 mM phosphate (1 M NaCl, pH 7). The column was then cleaned with 500 mM phosphate, pH 7. The experiment was monitored at 254 and 280 nm. The last peak to elute has a 254/280 ratio of about 2/1, indicating that it is composed mainly of DNA.

Example 2

The experiment was repeated as in Example 1, this time inserting a 10 CV decomplexant wash of 4 M urea, 20 mM Hepes, 20 mM MES, 5 mM calcium, pH 7, following sample loading. The column was then restored to native apatite by washing with 10 mM phosphate, eluted with a NaCl gradient, and cleaned with 500 mM phosphate as described above. The addition of the decomplexant wash modestly increased the amount of DNA eluted in the cleaning step, and thus the DNA content of the eluted IgG was lower.

Example 3

The experiment was repeated as in Example 1, this time inserting a 10 CV decomplexant wash of 2 M NaCl, 20 mM Hepes, 20 mM MES, 5 mM calcium, pH 7, following sample loading. The column was then restored to native apatite by washing with 10 mM phosphate, eluted with a NaCl gradient, and cleaned with 500 mM phosphate as described above. The addition of the decomplexant wash strongly increased the amount of DNA eluted in the cleaning step, and thus the IgG content of the eluted DNA was lower. This experiment highlights the ability of the NaCl to enhance the effectiveness of the apatite chromatography support itself as a decomplexing agent.

Example 4

The experiment was repeated as in Example 1, this time inserting a 10 CV decomplexant wash of 1.6 M NaCl, 3.2 M urea, 20 mM Hepes, 20 mM MES, 5 mM calcium, pH 7, following sample loading. The column was then restored to native apatite by washing with 10 mM phosphate, eluted with a NaCl gradient, and cleaned with 500 mM phosphate as described above. The addition of a decomplexant wash comprising two decomplexing agents increased the amount of DNA eluted in the cleaning step more than either urea or NaCl alone, and thus the DNA content of the eluted IgG was proportionately lower. This experiment highlights that combinations of decomplexants may be more effective than individual decomplexants.

Discussion

Comparing the elution patterns in each of the above experiments reveals in addition that decomplexant washes changed the elution pattern of non-antibody contaminants, while concurrently reducing contaminant peak sizes. This demonstrates the above-discussed point that decomplexant washes can dissociate "supercontaminants" into their individual consituents. Our results further suggest that some of these individualized contaminants may be removed entirely (eluted) during the decomplexant wash, thereby enhancing the purification to an even greater degree.

Comparing the elution patterns in each of the above experiments further indicates that decomplexant washes, by eliminating DNA fragments from the surface of IgG, restored IgG to its native charge characteristics. For example, comparing Example 1 with the decomplexant washes in Examples 2-4, the elution peak in Example 1 "leans" towards the right (relatively speaking) with the peak center occurring at 5-6 mS/cm higher conductivity, compared to the IgG peak following any of the decomplexant washes. This differential indicates that IgG:DNA complexes, by virtue of the strong calcium affinity of the DNA on their surfaces, elute from hydroxyapatite slightly later than uncomplexed IgG, thereby shifting the overall peak configuration to the right. When the DNA is removed the peak configuration reflects the elution characteristics of native IgG.

Example 5

Previous work with this antibody has shown that a cation exchange→anion exchange→native hydroxyapatite purification process, in which the hydroxyapatite was eluted under conditions identical to Example 1, failed to remove DNA and left the IgG in a highly aggregated state. Specifically, aggregates amounted to about a third of the total IgG and fragments about another third, and DNA in the final product was still present in excess of 40 ppm. In contrast, a chromatogram of the analytical size exclusion profile of this antibody purified by cation exchange and metal-derivatized hydroxyapatite under the conditions described in Example 4 illustrates that despite having been purified by only a 2-step process, it showed less contamination than the 3-step process (cation exchange→anion exchange→native hydroxyapatite purification process) and had substantially more antibody in monomeric form (greater than 90% monomer, less than 3% dimer, less than 1% aggregates, and no apparent fragments).

Discussion

For reasons previously not understood, aggregate removal on apatite chromatography supports using native hydoxyapatite is not always effective, creating a difficult and costly challenge for process developers. The experimental results shown in Example 4 show that the use of derivatized apatite and inclusion of a decomplexant wash gives apatite chromatography media the ability to remove aggregates even from "resistant" antibodies. In addition, experimental observations indicate that non-covalent aggregates are not actually removed, as with IgG purified by native hydroxyapatite in the absence of decomplexant, even though at least some IgG is restored to its native form. The use of decomplexants represents an improvement in recovery, with potentially valuable economic benefits. Inclusion of reducing agents in the complex-disociative wash may be able to restore native IgG even from covalent aggregates. These results suggest that DNA complexation plays a direct role in the formation and stabilization of aggregates, and further suggest that DNA removal itself may offer a novel and effective tactic for aggregate removal.

These results collectively indicate a mechanism of action illustrated by the following hypothetical example: IgG:DNA complexes are at least partially stable when initially applied to apatite supports. Application of decomplexing washes weakens the association between complexants but may not fully dissociate them. Because of its high affinity for apatite calcium however, the DNA component is attracted much more strongly to the calcium-derivatized apatite support than it is to the antibody. The combination of weakened complexation and strong attraction to the apatite cause the DNA to "abandon" the IgG and bind strongly to the apatite. Once bound, it cannot rejoin the IgG, so that when the IgG is eluted, the DNA remains behind, even if the apatite is restored before elution to its non-calcium-derivatized form. This model explains why apatite chromatography supports are uniquely qualified to practice the invention, and why the invention offers more effective DNA removal than other chromatography methods.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of purifying a target molecule from a biological sample, the method comprising in the following order,
   (a) contacting the sample comprising the target molecule and complexed contaminants to a metal cation-derivatized apatite solid support or a polycation-derivatized apatite solid support, wherein the metal cation is calcium, thereby non-covalently binding the target molecule to the solid support so as to provide a bound target molecule;

(b) washing the bound target molecule with an agent(s) that displaces the complexed contaminants from the target molecule under conditions in which the target molecule remains substantially bound to the solid support, wherein the agent(s) comprise urea, 0.5-2.0 M sodium chloride, or both; and (c) eluting the target molecule from the solid support, wherein the eluted target molecule is substantially free of complexed contaminants.

2. The method of claim 1, comprising washing the agent(s) from the solid support prior to the eluting step.

3. The method of claim 1, comprising converting the metal cation-derivatized apatite solid support or polycation-derivatized apatite solid support to a non-derivatized apatite between the washing step (b) and the eluting step (c) such that the solid support is a non-derivatized apatite solid support during the eluting step (c).

4. The method of claim 1, wherein the solid support is a metal cation-derivatized apatite solid support or a polycation-derivatized apatite solid support during the eluting step (c).

5. The method of claim 1, wherein the apatite is hydroxyapatite or fluorapatite.

6. The method of claim 5, wherein the apatite is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; hydroxyapatite CHT Type II, 80 micron; fluorapatite CFT Type I, 40 micron; and fluorapatite CFT Type II, 40 micron.

7. The method of claim 1, wherein the target molecule is selected from the group consisting of a protein, antibody, phosphoprotein, virus, and nucleic acid.

8. The method of claim 7, wherein the target molecule is an antibody.

9. The method of claim 7, wherein the nucleic acid is DNA or RNA.

10. The method of claim 1, wherein the complexed contaminants are selected from the group consisting of protein, nucleic acids, lipids, metal ions, sulfides, polysaccharides, and endotoxins.

11. The method of claim 1, wherein the agent is sodium chloride.

12. The method of claim 1, wherein the washing step (b) comprises contacting the solid support binding the target molecule with a solution comprising two or more different agents that displace the complexed contaminants.

13. The method of claim 12, wherein the two or more different agents comprise:
　i. urea and sodium chloride; or
　ii. urea and sodium chloride and cysteine.

14. The method of claim 1, wherein the complexed contaminants are non-covalently complexed with the target molecule.

15. The method of claim 1, wherein the complexed contaminants are covalently complexed with the target molecule.

16. The method of claim 1, wherein the complexed contaminants are covalently complexed with the target molecule via a disulfide bond and wherein said agents in the washing step (b) comprise a reducing agent in combination with at least one agent other than a reducing agent, thereby reducing the disulfide bond.

17. The method of claim 1, wherein the target molecule is eluted from the solid support while the complexed contaminants are bound to the solid support.

18. The method of claim 1, wherein the target molecule is eluted from the solid support after the complexed contaminants are eluted from the solid support.

19. The method of claim 18, wherein the target molecule is a nucleic acid and the contaminants comprise non-nucleic acid molecules.

20. The method of claim 1, wherein the target molecule is a protein and the contaminants comprise non-protein molecules.

21. The method of claims 1, wherein the target molecule is a protein and the contaminants comprise a protein other than the target molecule protein.

22. The method of claim 1, wherein the target molecule is a virus and the contaminants comprise non-virus molecules.

23. The method of claim 1, wherein the agent is urea.

24. The method of claim 10, wherein the complexed contaminants are nucleic acids.

* * * * *